US009063085B2

(12) United States Patent
McManus et al.

(10) Patent No.: US 9,063,085 B2
(45) Date of Patent: *Jun. 23, 2015

(54) METHODS AND SYSTEMS FOR ANALYZING SAMPLES

(71) Applicant: Materialytics, LLC, Harker Heights, TX (US)

(72) Inventors: Catherine E. McManus, Waynesville, MO (US); James W. Dowe, III, Richland Springs, TX (US); Tristan M. Likes, Fayetteville, NC (US); James W. Dowe, IV, Killeen, TX (US)

(73) Assignee: Materialytics, LLC, Harker Heights, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/184,781

(22) Filed: Feb. 20, 2014

(65) Prior Publication Data
US 2014/0185043 A1    Jul. 3, 2014

Related U.S. Application Data

(63) Continuation of application No. 13/760,349, filed on Feb. 6, 2013, now Pat. No. 8,699,022.

(60) Provisional application No. 61/595,903, filed on Feb. 7, 2012.

(51) Int. Cl.
*G01J 3/30*    (2006.01)
*G01J 3/36*    (2006.01)
(Continued)

(52) U.S. Cl.
CPC .............. *G01N 21/62* (2013.01); *G01N 21/63* (2013.01); *G06F 17/00* (2013.01); *G01N 21/718* (2013.01)

(58) Field of Classification Search
CPC ............... G01N 21/718; G01N 2021/3595; G01N 2021/1793; G01N 21/31
USPC .......................... 356/316, 318, 311, 306, 307
See application file for complete search history.

(56) References Cited

U.S. PATENT DOCUMENTS 4,097,239 A    6/1978 Patterson
4,776,690 A    10/1988 Quimby
(Continued)

FOREIGN PATENT DOCUMENTS

| WO | 2011/120086 | 10/2011 | |
| WO | WO 2011/130804 | 10/2011 | ............. G01N 21/63 |
| WO | 2012/087405 | 6/2012 | |

OTHER PUBLICATIONS

Notification of Transmittal of the International Search Report and the Written Opinion of the International Searching Authority for International Application No. PCT/US2014/024012 dated Jul. 28, 2014 (14 pages).

(Continued)

*Primary Examiner* — Tarifur Chowdhury
*Assistant Examiner* — Sunghee Y Gray
(74) *Attorney, Agent, or Firm* — Fish & Richardson P.C.

(57) ABSTRACT

This disclosure relates to a method for analyzing a sample of material. The method includes (a) converting a portion of the sample into a plasma multiple times; (b) recording a spectrum of electromagnetic radiation emitted in response to each of the sample conversions to define a sequence of spectra for the sample, in which each member of the sequence corresponds to the spectrum recorded in response to a different one of the sample conversions; (c) using an electronic processor to compare the sequence of spectra for the sample to a sequence of spectra for each of at least one reference sample in a reference library; and (d) using the electronic processor to determine information about the sample based on the comparison to the reference samples in the library.

29 Claims, 5 Drawing Sheets

(51) Int. Cl.
G01N 21/62 (2006.01)
G01N 21/63 (2006.01)
G06F 17/00 (2006.01)
G01N 21/71 (2006.01)

(56) References Cited

U.S. PATENT DOCUMENTS

| | | | |
|---|---|---|---|
| 5,798,822 | A | 8/1998 | Miyazaki et al. |
| 5,798,832 | A | 8/1998 | Hnilica et al. |
| 7,161,672 | B2 * | 1/2007 | Gornushkin et al. ......... 356/328 |
| 7,195,731 | B2 | 3/2007 | Jones |
| 7,228,239 | B1 | 6/2007 | Cetto |
| 7,298,475 | B2 * | 11/2007 | Gandhi et al. ................ 356/318 |
| 7,359,805 | B1 | 4/2008 | Cetto |
| 7,557,917 | B1 | 7/2009 | Beesley |
| 7,672,792 | B1 | 3/2010 | Cetto |
| 2002/0166960 | A1 | 11/2002 | Pronko et al. |
| 2003/0071216 | A1 | 4/2003 | Rabolt et al. |
| 2003/0234928 | A1 | 12/2003 | Lucas et al. |
| 2006/0172429 | A1 | 8/2006 | Nilsson et al. |
| 2007/0135999 | A1 | 6/2007 | Kolatt |
| 2007/0231921 | A1 | 10/2007 | Roder et al. |
| 2008/0100836 | A1 | 5/2008 | Hagler |
| 2008/0306346 | A1 | 12/2008 | Claus et al. |
| 2008/0306898 | A1 | 12/2008 | Tsypin et al. |
| 2009/0004644 | A1 | 1/2009 | Kiel et al. |
| 2009/0273782 | A1 | 11/2009 | Yoo et al. |
| 2009/0290151 | A1 | 11/2009 | Agrawal et al. |
| 2011/0042353 | A1 | 2/2011 | Menoni et al. |
| 2011/0100967 | A1 | 5/2011 | Yoo et al. |
| 2011/0237446 | A1 | 9/2011 | Treado et al. |

OTHER PUBLICATIONS

Harmon, Russell S. et al: "LIBS for landmine detection and discrimination", *Analytical and Bioanalytical Chemistry*, Springer, Berlin, DE, vol. 385, No. 6, pp. 1140-1148, May 25, 2006.
Lentjes et al: "Calculation and optimization of sample identification by laser induced breakdown spectroscopy via correlation analysis", *Spectrochimica Acta, Part B*: Atomic Spectroscopy, New York, NY, US, US, vol. 62, No. 1, pp. 56-62, Feb. 24, 2007.
International Search Report and the Written Opinion Issued in International Application No. PCT/US2013/024843 dated Jun. 7, 2013.
Abduriyim, A., et al., "Applications of laser ablation-inductively coupled plasma-mass spectrometry (LA-ICP-MS) to gemology", Gems & Gemology, 42(2), 98-118, 2006.
Abduriyim, A., "Determination of the origin of blue sapphires using laser ablation inductively coupled plasma mass spectrometry (LA-ICP-MS)", Journal of Gemology, v. 30, 23-36, 2006.
Abduriyim, A., et al., ""Paraiba"-type copper-bearing tourmaline from Brazil, Nigeria, and Mozambique: Chemical fingerprinting by LA-ICP-MS", Gems and Gemology, v. 42, p. 4-21, 2006.
Alvey, D.C., et al., "Laser-induced breakdown spectroscopy-based geochemical fingerprinting for the rapid analysis and discrimination of minerals: the example of garnet", Applied Optics, 49(13), C168-C180, 2010.
Anazano, J.M., et al., "Laser-induced breakdown spectroscopy for quantitative spectrochemical analysis of geological materials: Effects of the matrix and simultaneous determination", Analytica Chimica Acta, v. 575, p. 230-235, 2006.
Bailey, T., et al., "A note on distance-weighted k-nearest neighbor rules", IEEE Transactions System Man, Cybernetics, 8: 311-313, 1978.
Beran, A., et al., "OH in naturally occurring corundum", European Journal of Mineralogy, v. 18, p. 441-447, 2006.
Bermejo, S., et al., "Adaptive soft k-nearest neighbour classifiers", Pattern Recognition, 33 (12): 1999-2005, 2000.
Bol'shakov, A.A., et al., "Laser Induced Breakdown Spectroscopy in Industrial and Security Applications", Applied Optics, v. 49 (13), p. C132-C142, 2010.
Bol'shakov, A. A., et al., "Discrimination of Complex Substances with Laser-Induced Breakdown Spectroscopy", p. 1-7, (2009).
Bousquet, B., et al., "Towards quantitative laser-induced breakdown spectroscopy analysis of soil samples", Spectrochimica Act, v. 62, p. 1582-1589, 2007.
Breeding, C., et al., "Developments in gemstone analysis techniques and instrumentation during the 2000s", Gems & Gemology, 46: p. 241-257, 2010.
Bremner, D., et al., "Output-sensitive algorithms for computing nearest-neighbor decision boundaries", Discrete and Computational Geometry, 33 (4), p. 1-11, 2005.
Calligaro, T., et al., "Trace element fingerprinting of jewelry rubies by external beam PIXE", Nuclear Instruments and Methods, Bulletin, v. 150, p. 628-634, 1999.
Calvo del Castillo, et al., "Towards the differentiation of non-treated and treated corundum minerals by ion-beam-induced luminescence and other complementary techniques", Analytical and Bioanalytical Chemistry, v. 394, p. 1043-1058, 2009.
Chinni, R., et al., "Analysis of material collected on swipes using laser-induced breakdown spectroscopy", Applied Optics. 49, C143-C152, 2010.
Clegg, S.M., et al., "Multivariate analysis of remote laser-induced breakdown spectroscopy spectra using partial least squares, principal component analysis, and related techniques", Spectrochimica Acta Part B, v. 64, p. 79-88, 2009.
Coomans, D., et al., Alternative k-nearest neighbour rules in supervised pattern recognition, part 1. k-nearest neighbour classification by using alternative voting rules, Analytica Chimica Acta, 136, 15-27, 1982.
Cover, T.M., et al., "Nearest neighbor pattern classification", IEE Transactions on Information Theory, 13 (1): 21-27, 2006.
Cremers, D.A., Handbook of Laser-Induced Breakdown Spectroscopy, John Wiley & Sons, Ltd., Chapter 1-6, 2006.
Death, D.L., et al., "Multi-element and mineralogical analysis of mineral ores using laser induced breakdown spectroscopy and chemometric analysis", Spectrochimica Acta, v. 64, 9. p. 1048-1058, 2009.
De Giacomo, A., et al., "Laser induced breakdown spectroscopy on meteorites", Spectrochimica Acta, v. 62, p. 1606-1611, 2007.
DeLucia, F.C., et al., "Laser-induced breakdown spectroscopy (LIBS) a new versatile chemical sensor technology for Hazard Material Detection", IEEE, v. 5, p. 681-689, 2005.
De Maesschalck, R., et al., "The mahalanobis distance", Chemometrics and Intelligent Laboratory Systems, 50: 1-18, 2000.
Denison, D.G.T., "Bayesian Methods for Nonlinear Classification and Regression", Chichester, England: Wiley, 2002, pp. 2-44 and 209-220.
Doucet, F.R., et al., "Determination of isotope ratios using laser-induced breakdown spectroscopy in ambient air at atmosphere pressure for nuclear forensics", Journal of Analytical Atomic Spectrometry, v. 26 p. 536-541, 2011.
DuToit, G., et al., "Continuing market observations and update including the emergence of larger size stones", Feb. 3, 2012, from Beryllium Treated Blue Sapphires Web Site: http://www.giathai.net/pdf/Beryllium_diffused_blue_sapphires_at_June_26th_2009.pdf.
Dyar, M., et al., Strategies for Mars remote Laser-Induced Breakdown Spectroscopy analysis of sulfur in geological samples, Spectrochimica Acta Part B v. 66 p. 39-56, 2011.
Fisher, R., "The use of multiple measurements in taxonomic problems", Annals Eugenics, 7 (2): 179-188.
Fix, E., et al., "Discriminatory Analysis, Nonparametric Discrimination: Consistency Properties", Technical Report 4: USAF School of Aviation Medicine, Texas: Randolph Field, 1951.
Fretz, R., et al., "Update: multinational Listeriosis outbreak due to 'Quargel', a sour milk curd cheese, caused by two different L. Monocytogenes Serotype 1/2a Strains", 2009-2010: Eurosurveillance, 15 (16).
Fukunaga, K., et al., "k-Nearest Neighbor Bayes-Risk Estimation", IEEE Transactions on Information Theory, 21 (3): 285-293, 1975.

(56) References Cited

OTHER PUBLICATIONS

Galiová, M., et al., "Multielemental analysis of prehistoric animal teeth by laser-induced breakdown spectroscopy and laser ablation inductively coupled plasma mass spectroscopy", Applied Optics, v. 49, p. 191-199, 2010.
Giuliani, G., et al., "Oxygen isotope composition as a tracer for the origins of rubies and sapphires", Geology, 33(4), 249-252, 2005.
Gnanadesikan, R., et al., "Robust estimates, residuals, and outlier detection with multiresponse data", Biometrics, 28: 81-124, 1972.
Gubelin—GEM LAB—Inclusions, (n.d). Gubelin—GEM LAB. Retrieved Feb. 3, 2012, from http://www.gubelingemlab.ch/About-Gemstones-and-Pearls/ Inclusions.php.
Günther, D., et al., "Laser ablation-inductively coupled plasma-mass spectrometry: a new way of analyzing gemstones", Gems & Gemology, v. 35, p. 60-161, 1999.
Guvenir, H., et al., "Learning differential diagnosis of Erythemato-Squamous diseases using voting feature intervals: Artificial Intelligence in Medicine", 13 (3): 147-165.
Hahn, D.W., et al., "Understanding and Mitigating Matrix Effects in Laser-induced Plasmas", p. 36, retrieved Feb. 3, 2012, from North American Symposium on LIBS Web Site: http://www.icet.msstate.edu/naslibs2011/pro3NASLIBS11.pdf. Jul. 28, 2008.
Hall, P., Park, et al., "Choice of neighbor order in nearest-neighbor classification", Annals of Statistics, 36 (5): 2135-2152, 2008.
Harmon, R.S., et al., "Can the provenance of the conflict minerals columbite and tantalite be ascertained by laser-induced breakdown spectroscopy", Anal Bioanal Chem (2011) 400:3377-3382.
Harmon, R.S., et al., "LIBS analysis of geomaterials: Geochemical fingerprinting for the rapid analysis and discrimination of minerals", Applied Geochemistry, v. 24, p. 1125-1141, 2009.
Harmon, R.S., et al., "Laser-induced breakdown spectroscopy—an emerging chemical sensor technology for field-portable, real-time geochemical, mineralogical, and environmental applications", Applied Geochemistry, 21, 730-747, 2006.
Hellman, M., "The nearest neighbor classification rule with a reject option", IEEE Transactions System Man Cybernation, 6 (3): 179-185, 1970.
Inclusion—Wikipedia, the free encyclopedia. (n.d.). Wikipedia: The Free Encyclopedia. Retrieved Feb. 3, 2012, from http://en.wikipedia.org/wiki/Inclusion.
Johnson, M.L., "Durability testing of filled emeralds", Gems & Gemology, v. 43, No. 2, p. 120-137, 2007.
Joseph, D., et al., "Characterization of gem stones (rubies and sapphires) by energy-dispersive X-ray fluorescence Spectrometry", X-Ray Spectrom. v. 29, p. 147-150, 2002.
Jurado-Lo 'pez, A., et al., "Rank correlation of laser-induced breakdown spectroscopic data for the identification of alloys used in jewelry manufacture", Spectrochimica Acta Part B 58, 1291-1299, 2003.
Kane, R.E., et al., "A gemological pioneer: Dr. Edward J. Gubelin", Gems & Gemology, v. 41, p. 298-327, 2005.
Keller, J., et al., "A fuzzy k-nearest neighbor algorithm", IEEE Transactions System Man Cybernation, 15 (4): 580-585, 1985.
Krzemnicki, M., et al., "A new method for detecting be diffusion-treated sapphires: laser-induced breakdown spectroscopy (LIBS)", Gems & Gemology, 40(4), 314-322, 2004.
Liddicoat, R.T., "The country of origin question", Gems & gemology, v. 26, p. 247, 1990.
Likes, T., et al., "Use of the Materialytics Sequencing System (M2S) to Solve Complex Geochemical Problems: The Case of Emerald Provenance", Materialytics, LLC 2011.
Likes, T., et al., "Use of Laser-Induced Breakdown Spectroscopy (LIBS) to Solve Complex Geochemical Problems: The Case of Emerald Provenance", Geological Society of America Annual Meeting, 2011.
Mahalanobis, P., "On the generalized distance in statistics", Proceedings of the National Institute of Sciences of India 2 (1): 49-55, 1936.
Mao, X., B, et al., "Laser ablation molecular isotopic spectrometry" parameter influence on boron isotope measurements, Spectrochimica Acta Part B 66, 604-609, 2011.
Mao, X., et al., "Laser ablation molecular isotopic spectrometry: strontium and its isotopes", Spectrochimica Acta Part B, Atomic Spectroscopy, 2011.
"Materialytics Presentation of Findings", Compatibility Model, Feb. 8, 2011.
McManus,C.E., et al., "Determining the Provenance of Gemstones Using the Materialytics Sequencing System (M2S)", GIA Symposium 2011: Advancing the Science and Business of Gems, Geological Society of America Annual Meeting, Oct. 2011.
McManus, C.E., et al., "Assessment of Provenance of Conflict Minerals Using the Materialytics Sequencing System (M2S)", Materialytics, LLC 2011.
McManus, C.E., et al., "Assessment of provenance of conflict minerals using laser-induced breakdown spectroscopy (LIBS)", Geological Society of America Abstracts with Programs 43(5), 242, 2011.
McManus, C.E, et al., "Determining the provenance of gemstones using Materialytics Sequencing System (M2S)", Gems & Gemology, 47(2):155-156, 2011.
McManus, C.E., et al., "Provenance determination of tourmaline using the Materialytics Sequencing System (M2S)", North American Symposium on Laser Induced Breakdown Spectroscopy Program and Abstracts 3, 21, 2011.
McManus, C.E., et al., "Use of laser induced breakdown spectroscopy in the determination of gem provenance: beryls", Applied Optics, v. 47, No. 31, p. G72-G79, 2008.
McManus, C.E., et al., "LIBS Analysis of GemBeryls: Single-Pulse, Double-Pulse, and Provenance Determination", [abstr.], GoldSchmidt Conference, 2007.
McManus, C.E., et al., "Trace element variability in beryl using laser induced breakdown spectroscopy (LIBS): Implications for determining provenance", [Master's Thesis], Las Cruces, New Mexico State University, 187 p. 2007.
McManus, C.E., et al., "LIBS analysis of gem beryls: Analytical methodology and provenance", Pacifichem, v. 815, session 979, No. 12, 2005.
McManus, C.E., et al., "Trace element geochemistry of gem beryl", Goldschmidt Conference Abstracts, A281 2005.
McManus, C.E., et al., "Trace element concentrations of pegmatite gems: tracers of petrogenesis and terrorist funding", Geological Society of America Abstracts with Programs, 36(5), 226, 2004.
McMillan, N.J., et al., "Correlation of limestone beds using laser-induced breakdown spectroscopy and chemometric analysis", Applied Optics, v. 51, No. 7, p. B213-B222, 2012.
McMillan, N.J., et al., Laser Induced Breakdown Spectroscopy: A New Paradigm in Geochemical Analysis, Geological Society of America, v. 41, No. 6, p. 12, 2009.
McMillan, N.J., et al., "Laser-induced breakdown spectroscopy analysis of minerals: Carbonates and silicates", Spectrochimica Acta Part B, v. 62, p. 1528-1536, 2007.
McMillan, N.J., et al., "Laser-induced breakdown spectroscopy analysis of complex silicate minerals—beryl", Analytical and Bioanalytical Chemistry, No. 216, v.385:2, p. 263-271, 2006.
McMillan, N.J., et al., "What laser-induced breakdown spectroscopy can tell us about mineral composition", The beryl case study, Geological Society of America Abstracts with Programs, 38, 547, 2006.
Melcher, F., et al., "Fingerprinting of conflict minerals: Columbine-Tantalite ("Coltan") ores", SGA News, pp. 1 and 7, 2008.
Miziolek, A.W., et al., "Laser-induced breakdown spectroscopy (LIBS) fundamentals and applications", Cambridge: Cambridge University Press, pp. 1-367, 2006.
Multari, R. A, et al., "The use of laser-induced breakdown spectroscopy (LIBS) for distinguishing between bacterial pathogen species and strains", Applied Spectra, 64(7), 750-759, 2010.
Rehse, S., et al., "Towards the clinical application of laser-induced breakdown spectroscopy for rapid pathogen diagnosis: the effect of mixed cultures and sample dilution on bacterial identification", Applied Optics. 49(13), C27-C35, 2010.
Remus, J.J., et al., "Advanced signal processing analysis of laser-induced breakdown spectroscopy data for the discrimination of obsidian sources", Appl. Optics, 2012, 51, B65-B73, 2012.
Remus, J.J., et al., "Archaeological applications of laser-induced breakdown spectroscopy: an example from the Coso Volcanic Field,

(56) References Cited

OTHER PUBLICATIONS

California, using advanced statistical signal processing analysis", Applied Optics / vol. 49, No. 13 / May 1, 2010.
Remus, J.J., et al., "Robust Validation of Pattern Classification Methods for Laser-Induced Breakdown Spectroscopy", Applied Optics, vol. 51 (7), pp. B49-B56, 2012.
Rinke, C.N., et al., "Discriminant analysis in the presence of interferences: Combined application of target factor analysis and a Bayesian soft-classifier", Analytica Chimica Acta 753 (2012) 19-26.
Robinson, J.W., "Practical Handbook of Spectroscopy", Boca Raton: CRC Press, 1991.
Russo, R.E., et al., "Laser plasma spectrochemistry", J. Anal. At. Spectrom, 2011, 26, 1596.
Securities and Exchange Act of 1934, Section 13, Title XV—Miscellaneous Provisions, Section 1502: Conflict Minerals, 2010.
Securities and Exchange Commission. 17 CFR—Parts 229 and 249. Release No. 34-63547; File No. S7-40-10. RIN 3235-AK84: Conflict Minerals, 2010.
Sharp, Z.D., "A laser-based microanalytical method for the in situ determination of oxygen isotope ratios of silicates and oxides", Geochimica et Cosmochimica Acta, v. 54, p. 1353-1357, 1990.
Shigley, J.E., et al., "Gem Localities of the 1990s", Gems and Gemology, Winter 2000, p. 292-335, 2000.
Shughrue, K., et al., "Analysis of the 'Conflict Minerals' Columbite-Tantalite Using Laser-induced Breakdown Spectroscopy (LIBS)", Applied Spectra Inc—May 27, 2011.
Sirven, J.B., et al., "Laser-induced breakdown spectroscopy of composite samples: Comparison of advanced chemometrics methods", Analytical Chemistry, v. 78, p. 1462-1469, 2006.
Smith, C.A., et al., "Pu-239/Pu-240 isotopic ratios determined using high resolution emission spectroscopy in laser-induced plasma", Spectrochimica Acta, v. 57, p. 929-937, 2002.
Stravropoulos, P., et al., "Calibration measurements in laser-induced breakdown spectroscopy using nanosecond and picosecond lasers", Spectrochimica Acta Part B, v. 59, p. 1885-1892, 2004.
Terrell, D., et al., "Variable kernel density estimation", Annals of Statistics, 20 (3), 1236-1265, 1992.
Toussaint, G., "Geometric Proximity Graphs for Improving nearest neighbor methods in Instance-Based Learning and Data Mining", International Journal of Computation Geometry & Applications, vol. 15, No. 2 (2005) 101-150.
Tucker, J.M., et al., "Optimization of laser-induced breakdown spectroscopy for rapid geochemical analysis", Chemical Geology, v. 277, p. 137-148, 2010.
Viswanath, P., "An improvement to k-nearest neighbor classifier", Dept. of Comput. Sci. & Eng., Rajeev Gandhi Memorial Coll. of Eng. & Technol., Nandyal, India, pp. 227-231, Sep. 22-24, 2011.
Wang, W., et al., "Applications to diamond testing", A new analytical technique: LA-ICP-MS, Rappaport Diamond Report, v. 26, p. 177-181, 2003.
Watling, R.J., et al., "Analysis of diamonds and indicator minerals for diamond exploration by laser ablation-inductively coupled plasma mass spectrometry", Analst, v. 120, p. 1357-1364, 1995.
Yetter, K.A., et al., "Provenance of Rubies and Sapphires: An Application of Laser-Induced Breakdown Spectroscopy (LIBS) and Advanced Chemometrics for the Gem Industry," GIA Symposium 2011: Advancing the Science and Business of Gems, May 2011.
Yetter, K.A., "Determining provenance of corundum using laser-induced breakdown spectroscopy (LIBS) and chemometric analysis", [Master's Thesis], Las Cruces, New Mexico State University, 140 p, 2011.
Yetter, K.A., et al., "Provenance of gem corundum", A global LIBS study [abstr.]: Goldschmidt Geochemical Conference 2010, Knoxville, TN, 2010.
Yetter, K.A., "Provenance of Rubies and Sapphires: An Application of Laser-Induced Breakdown Spectroscopy (LI BS) and advanced Chemometrics for the Gem Industry", 5th International Gemological Symposium, Gems & Gemology, p. 7, 2011.

\* cited by examiner

METHODS AND SYSTEMS FOR ANALYZING SAMPLES

CROSS-REFERENCE TO RELATED APPLICATIONS

This application is a continuation of U.S. application Ser. No. 13/760,349, filed on Feb. 6, 2013, which claims priority to U.S. Provisional Application No. 61/595,903, filed on Feb. 7, 2012. The contents of the parent applications are hereby incorporated by reference in their entirety.

TECHNICAL FIELD

This disclosure relates to methods and systems for analyzing samples of materials, and more particularly to methods and systems for determining the identity, place of origin, and/or treatment history of an unknown sample.

BACKGROUND

Provenance determination of materials (e.g., minerals) is useful for a variety of reasons. For example, materials from one location may be more valuable than those from another location. In addition, laws restricting the sale of materials from certain areas may exist due to geopolitical concerns. Currently, distinguishing between particular conflict ore deposits (e.g., columbite and tantalite) requires a combination of mineralogical, geochemical and geochronological analyses, which can be both time consuming and catastrophically destructive to the sample. In the case of rare and highly valuable materials, non-destructive analytical tools are typically necessary to preserve the integrity of the sample.

As it currently stands, non-destructive origin determination is largely based on a combination of human observations and data collected from advanced analytical instrumentation. Final determination decisions typically fall to the uncertain and sometimes varying opinions of research scientists. Techniques traditionally used for origin determination include Raman and Luminescence Spectroscopy, X-ray Radiography, Tomography, Energy-Dispersive X-Ray Fluorescence (EDXRF), and Scanning Electron Microscope Energy-Dispersive Spectroscopy (SEM-EDS). Secondary Ion Mass Spectrometry (SIMS) and Laser-Ablation Inductively Coupled Plasma Mass Spectrometry (LA-ICP-MS) have also recently been applied to provenance determination studies. Each of the above techniques offers both advantages and disadvantages.

SUMMARY

This disclosure is based on the unexpected discovery that the entire emission spectrum of a sample of a physical material (e.g., a gemstone) can be used to determine its place of origin more accurately than a conventional method using only a portion of the emission spectrum of a sample. In addition, this disclosure is based on the unexpected discovery that variations in the emission spectrum of a physical material resulting from sample non-homogeneity and/or different excitation conditions should not be discarded as noise or averaged, but instead can be used to more accurately determine the identity of the sample.

The methods described herein are based on an assumption that every material, natural or man-made, bears traces of the materials and processes involved in its creation. Every sample of material, if examined in sufficient detail, is different from every other sample. The methods described herein use those traces of formation to classify samples according to their similarities and differences.

Provenance determination is useful for a variety of reasons, such as determining the value of the material (e.g., a mineral) or whether a material (e.g., a manufactured material) has been made to its specifications. "Provenance" mentioned herein can refer to geographical sites of discovery in the case of natural materials such as minerals, but can also refer to a particular factory, process, or manufacturer in the case of man-made materials. Provenance determination of man-made materials allows for the identification of counterfeit products and/or substandard products.

In one aspect, this disclosure features a method for analyzing a sample. The method includes (a) converting a portion of the sample into a plasma multiple times; (b) recording a spectrum of electromagnetic radiation emitted in response to each of the sample conversions to define a sequence of spectra for the sample, in which each member of the sequence corresponds to the spectrum recorded in response to a different one of the sample conversions; (c) using an electronic processor to compare the sequence of spectra for the sample to a sequence of spectra for each of multiple reference samples in a reference library; and (d) using the electronic processor to determine information about the sample based on the comparison to the multiple reference samples in the library.

In another aspect, this disclosure features a system for analyzing a sample. The system includes (a) an excitation source for converting a portion of the sample into a plasma multiple times; (b) a spectrometer configured to record a spectrum of electromagnetic radiation in response to each of the sample conversions to define a sequence of spectra for the sample, in which each member of the sequence corresponds to the spectrum recorded in response to a different one of the sample conversions; and (c) an electronic processor configured to compare the sequence of spectra for the sample to a sequence of spectra for each of multiple reference samples in a reference library and determine information about the sample based on the comparison to the multiple reference samples in the library.

Alternatively, in each of these aspects, there can be as a few as one reference sample in the reference library, in which case, the electronic processor can determine the information about the sample based on the comparison to the sequence of spectra in the one reference sample in the library. This is appropriate when the desired information about the sample being analyzed is, for example, a simple verification or authentication that the sample being analyzed does correspond, or does not correspond, to this single reference sample.

Embodiments with respect to any of these four aspects can include one or more of the following features.

In some embodiments, a pulse of electromagnetic radiation is used to convert the sample into the plasma for each of the multiple times. In some embodiments, the pulse of electromagnetic radiation can be derived from a laser, an ion beam, an electron beam, or an arc discharge. For example, the pulse of electromagnetic radiation can be derived from a laser and causes laser-induced breakdown of the sample.

In some embodiments, the sample is a solid (e.g., a gemstone, a metal, a manufactured material, such as a manufactured metal alloy, or a biological material). In certain embodiments, the sample is a liquid (e.g., the sample is blood, urine, oil, or water).

In some embodiments, the one or more reference samples are metal alloys having a common elemental composition and different processing protocols, such as different heat treatments.

In some embodiments, the sample being analyzed and the one or more reference samples can be metal alloys having a common elemental composition, and wherein the information determined by the electronic processor is whether the sample being analyzed has been subjected to a specific processing protocol corresponding to one of the reference samples.

In some embodiments, the conversion of the sample into the plasma causes the sample to emit electromagnetic radiation indicative of atomic emissions. In certain embodiments, the conversion of the sample into the plasma further causes the sample to emit electromagnetic radiation indicative of one or more of isotopic emissions, molecular emissions, molecular isotopic emissions, and spectral interference between atomic emissions from different atoms in the sample.

In some embodiments, each spectrum is recorded with a spectral resolution sufficient to resolve the emission of electromagnetic radiation corresponding to atomic emission and one or more of isotopic emission, molecular emission, molecular isotopic emission, and spectral interference between atomic emissions from different atoms. For example, each spectrum can be measured with a spectral resolution containing at least 10,000 channels. As another example, each spectrum can be measured with a spectral resolution finer than 0.1 nm, and preferably finer than 0.06 nm.

In some embodiments, each spectrum is measured over a range including from 195 nm to 1005 nm.

In some embodiments, members of the sequence for the sample correspond to the spectra recorded in response to different parameters for the pulse of electromagnetic radiation used to convert the portion of the sample into the plasma during the multiple times (e.g., multiple excitations). For example, the different parameters can include different pulse energies, different pulse durations, different pulse wavelengths, or combinations thereof.

In some embodiments, members of the sequence for the sample correspond to the spectra recorded in response to different incident locations on the sample for the pulse of electromagnetic radiation used to convert the portion of the sample into the plasma during the multiple times (e.g., multiple excitations). For example, the different incident locations can be sufficient to characterize heterogeneity in the atomic composition of the sample. In some embodiments, the different locations are separated from one another by at least 10 µm. In some embodiments, the different incident locations include at least 10 different locations (e.g., at least 15 different locations or at least 64 different locations).

In some embodiments, members of the sequence for the sample correspond to the spectra recorded in response to combinations of different parameters for the pulse of electromagnetic radiation used to convert the portion of the sample into the plasma during the multiple times (e.g., multiple excitations) and different incident locations on the sample for the pulse of electromagnetic radiation used to convert the portion of the sample into the plasma during the multiple times.

In some embodiments, the sequence of spectra for the sample can include members corresponding to all of the different spectra recorded for the sample during the multiple times (e.g., multiple excitations). As used herein, each "member" corresponds to a unique spectrum in the sequence of spectra. The set of such members define the "constituent" spectra for the sequence.

In some embodiments, the electronic processor can determine the members of the sequence of spectra for the sample by using a cluster technique. Such analysis can be applied to the sequence of spectra for the sample being analyzed and/or to the sequence of spectra for any of the reference samples.

In some embodiments, the comparison by the electronic processor comprises comparing a probability distribution for the members of sequence of spectra in the sample being analyzed to a probability distribution for the members of the sequence of spectra for each of the reference samples. For example, the probability distribution for the sample being analyzed can be represented as a histogram indicating the number of times each member occurs in the sequence of spectra for the sample being analyzed and the probability distribution for the members of each reference sample can be represented as a histogram indicating the number of times each member occurs in the sequence of spectra for each reference sample.

In some embodiments, the comparison by the electronic processor can include identifying a degree to which the sequence for the sample matches a sequence for each of at least some of the reference samples in the library. For example, identifying a degree can include (a) comparing each spectrum in the sequence for the sample to the different spectra in the library to identify the different spectra from the library most likely to match the spectra in the sequence for the sample; (b) identifying which reference samples from the library comprise all of the identified spectra; and (c) identifying a degree to which the sequence for the sample matches a sequence for each of the identified reference samples. In some embodiments, the electronic processor uses a nearest neighbor algorithm to perform one or both of the above identifying steps.

In another example, identifying the degree to which the sequence for sample matches a sequence for each of the reference samples comprises comparing a probability distribution for the members of the sample being analyzed to a probability distribution for the members of the sequence of spectra for each of the reference samples.

In some embodiments, the reference library is made by (a) providing information about the identity of each reference sample; (b) converting a portion of each reference sample into a plasma multiple times; and (c) recording a spectrum of electromagnetic radiation emitted from each reference sample in response to each of the reference sample conversions to define a sequence of spectra for each reference sample, wherein each member of the reference sample sequence corresponds to the spectrum recorded in response to a different one of the reference sample conversions. For example, members of each reference sample sequence correspond to the spectra recorded in response to combinations of different parameters for a pulse of electromagnetic radiation used to convert the portion of each reference sample into the plasma during the multiple times (e.g., multiple excitations) and different incident locations on each reference sample for the pulse of electromagnetic radiation used to convert the reference sample into the plasma during the multiple times.

In some embodiments, the information about the sample can include an identity or a provenance for the sample.

Other features and advantages of the disclosure will be apparent from the description, drawings, and claims.

DESCRIPTION OF DRAWINGS

Like reference symbols in the various drawings indicate like elements.

DETAILED DESCRIPTION

In general, this disclosure relates to methods and systems for analyzing a sample (e.g., to determine the identity and/or place of origin of the sample) by using the entire emission spectrum of the sample. In some embodiments, determining the identity of a sample can include determining whether a sample is manufactured according to a certain specification.

In some embodiments, the methods disclosed herein include acquiring one or more emission spectra of an unknown sample (i.e., a sample with an unknown place of origin or an unknown identity) and comparing the acquired spectra with the spectra of each reference sample (i.e., a sample with a known place of origin or a known identity) in a reference library. The place of origin or the identity of the unknown sample can then be determined when its spectra match (i.e., has sufficient similarity to) those of one or more reference samples in the library. In some embodiments, the library can include only one reference sample. In such embodiments, the methods disclosed herein can be used to verify whether the unknown sample is the same as, or different from, the reference sample (e.g., for verification or authentication).)

In general, the samples that can be analyzed by the methods disclosed herein can include any suitable materials, such as a geological material (e.g., minerals, gemstones, rocks, meteorites, or metals), a manufactured material (e.g., machined metal parts, cast metal parts, or pharmaceuticals), or a biological material (e.g., pathogens, bacteria, viruses, foods, or woods). Exemplary minerals include beryl, corundum, tourmaline, diamond, gold, wolframite, cassiterite, and columbite and tantalite (COLTAN). Exemplary gemstones include diamonds, emeralds, rubies, and sapphires. Exemplary rocks include limestones, marbles, and granites. In some embodiments, the samples that can be analyzed by the methods disclosed herein can be an inorganic material (e.g., gemstones) or an organic material (e.g., apples or oranges). In some embodiments, the samples that can be analyzed by the methods disclosed herein are solid samples or liquid samples (e.g., blood, urine, oil, or water).

In one application, the sample being analyzed and the one or more reference samples can be manufactured parts (e.g., metal alloys) that are subject to different processing conditions (e.g., different heat treatments). In such cases, the elemental compositions of the parts may be the same, but the different processing conditions cause the materials to have different properties. The techniques disclosed herein can distinguish between such parts.

Figure 1:
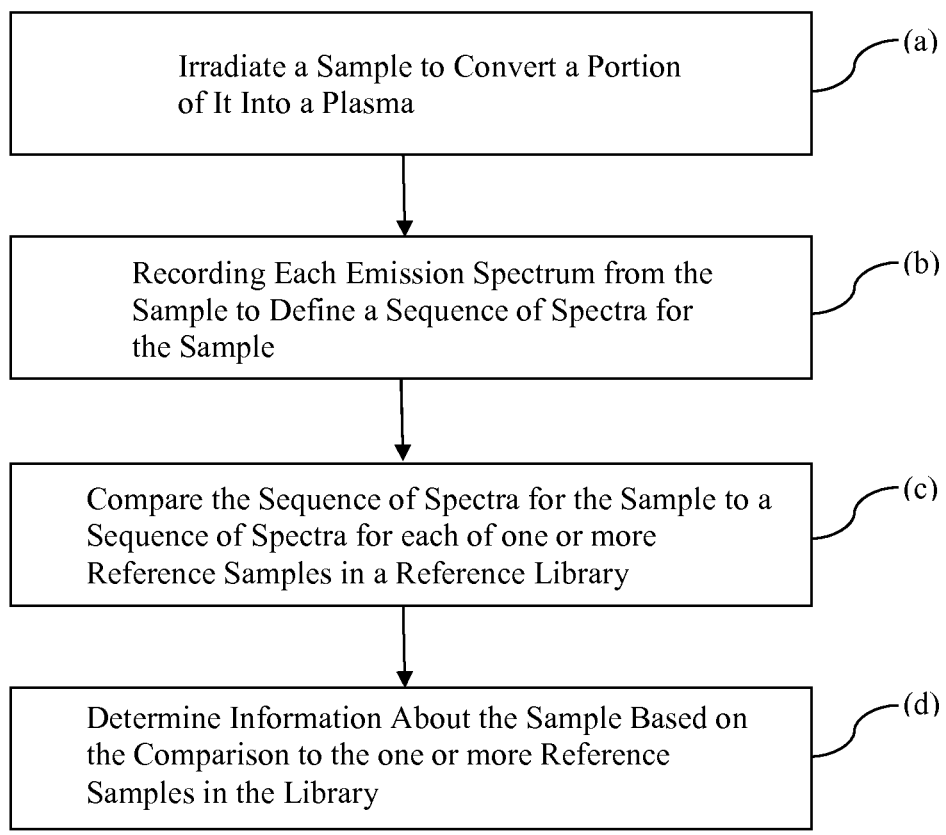
FIG. 1 is a flow chart showing a series of exemplary steps for comparing a sample to the reference samples in a reference library to obtain information about the sample.

FIG. 1 is a flow chart showing a series of exemplary steps for comparing a sample with the reference samples in a reference library to obtain information about the sample. As shown in FIG. 1, the methods disclosed herein can include the following steps: (a) converting a portion of a sample into a plasma multiple times; (b) recording a spectrum of electromagnetic radiation emitted in response to each of the sample conversions to define a sequence of spectra for the sample, in which each member of the sequence corresponds to the spectrum recorded in response to a different one of the sample conversions; (c) using an electronic processor to compare the sequence of spectra for the sample to a sequence of spectra for each of multiple reference samples in a reference library; and (d) using the electronic processor to determine information about the sample based on the comparison to the multiple reference samples in the library.

Step (a) can be performed by irradiating a pulse of electromagnetic radiation to the sample. In general, the electromagnetic radiation has sufficient energy to convert a portion of the sample into a plasma. Exemplary electromagnetic radiations include a laser beam (e.g., a 266 nm, 355 nm, 532 nm, or 1064 nm laser beam), an ion beam, an electron beam, and an arc discharge. Without wishing to be bound by theory, it is believed that the plasma thus formed contains various excited atomic elements, which emit electromagnetic radiations when these atomic elements return to a lower energy state. In some embodiments, the electromagnetic radiations are indicative of atomic emissions. In some embodiments, the electromagnetic radiations can further include those indicative of one or more of isotopic emissions, molecular emissions, molecular isotopic emissions, and spectral interference between atomic emissions from different atoms in the sample.

As used herein, the phrase "atomic emission" refers to emission of an electromagnetic radiation by an atomic element (e.g., a metal element such as Na or Mg) in a sample. Conventionally, atomic emissions have been used as the primary signals in an element analysis measurement to determine the place of origin of a sample, while the other emissions (e.g., isotopic emissions or molecular emissions) have been generally discarded as noise. For example, a conventional method typically selects a part of an emission spectrum (e.g., by using algorithms such as Partial Least Squares (PLS) or Principle Component Analysis (PCA)), or average a number of spectra to reduce what is assumed to be noise. By contrast, the methods disclosed herein rely on the entire emission spectra acquired from a sample to determine its place of origin. Without wishing to be bound by theory, it is believed that the emissions other than atomic emission (e.g., isotopic emissions, molecular emissions, or molecular isotopic emissions) represent "sequences" (or a petrogenetic signature) of a reference or unknown sample and should be included in the data analyses described herein to determine the place of origin of unknown samples. Further, without wishing to be bound by theory, it is believed that the minerals of the same type can have different "sequences" that vary depending on their places of origin (e.g., from countries to countries, from deposits to deposits, from mines to mines, and from zones to zones) and the environmental conditions (e.g., weathering, hydrothermal alternation, and local tectonic stresses) of their places of origin. Thus, without wishing to be bound by theory, it is believed that by using the entire emission spectra acquired from a sample (which can include the above-discussed additional emissions, as well as spectral interferences among these emissions and potentially other yet unidentified features), one can determine the place of origin of an unknown sample more accurately than conventional methods.

As used herein, the phrase "molecular emission" refers to emission of an electromagnetic radiation by a molecule (e.g., $H_2O$ or $CO_2$) in a sample. The phrase "isotopic emission" refers to emission of an electromagnetic radiation by an isotope of an atomic element (e.g. deuterium and hydrogen, $^{235}U/^{238}U$, or $^{10}B/^{11}B$) in a sample. Isotopic emissions within spectra are generally small. For example, the isotopic shift between $^{235}U/^{238}U$ at the emission line at 424.412 nm is 0.025 nm. As another example, the isotopic shift between $^{239}Pu$ and $^{240}Pu$ at the emission line of 594.522 nm is 0.005 nm and the isotopic shift between $^{10}B$ and $^{11}B$ at the emission line of 208.889 nm is 0.002 nm. It has been shown by Laser Ablation Molecular Isotopic Spectrometry (LAMIS) that the isotopic shifts found in molecular spectra are significantly larger than those of isotopic (atomic) spectra. For example, the molecular isotopic shift for $^{10}B^{16}O$ and $^{11}B^{16}O$ is 0.73 nm, which is significantly larger than the isotopic shift for $^{10}B$ and $^{11}B$ when they are not bonded to O. These isotopic shifts and molecular isotopic shifts are usually so small relative to the total intensity of the emitted radiation from a sample that they are traditionally disregarded as noise. However, as the methods disclosed herein utilize the entire emission spectrum of a sample, these small shifts are retained during data analyses when comparing the spectra collected from an unknown sample to the reference samples in a library.

As used herein, the phrase "spectral interference" refers to incomplete isolation of the radiation emitted by an analyte from other radiations detected by an instrument. As an example, when using the methods disclosed herein to analyze the mineral beryl, the element Be can have spectral interference with V, Ti, Fe, Cr, Mg, and Mn, the element Al can have spectral interference with Mg, V, Ca, Ti, Cr, Fe, and Mn, and the element Si can have spectral interference with Cr, Fe, Mg, V, Al, and Mn. These spectral interferences may cause an inaccurate representation of the chemical composition of the sample tested. Thus, traditionally, spectral interferences can be problematic in analyzing the chemical composition of a sample (especially in a quantitative measurement). By contrast, when used to determine the place of origin of an unknown sample, the methods disclosed herein can utilize the information contained in the spectral interference as these methods involve comparing the entire spectra acquired from the unknown sample with the entire spectra acquired from each of the reference samples in a library, and therefore are not concerned about the absolute intensities of the radiations emitted from the reference and unknown samples.

In general, step (a) in the methods disclosed herein includes irradiating a sample with electromagnetic radiation (e.g., laser) multiple times (e.g., at least 20 times, at least 30 times, at least 40 times, at least 60 times, or at least 80 times). In some embodiments, a sample is irradiated with electromagnetic radiation at multiple locations (e.g., at least 10 locations, at least 15 locations, at least 20 locations, at least 30 locations, at least 40 locations, at least 60 locations, or at least 120 locations) and up to as many as 240 locations or more. In some embodiments, a sample is irradiated with electromagnetic radiation multiple times at each of the above locations (e.g., at least twice or at least three times at each location). Without wishing to be bound by theory, it is believed that a sample (e.g., a mineral) can be heterogeneous both laterally and vertically on a microscopic scale. In addition, different pulses of electromagnetic radiation can have different energy intensities and therefore can produce different emission spectra. Thus, without wishing to be bound by theory, it is believed that by irradiating a sample at multiple locations and multiple times at each of these multiple locations and then collecting the spectra produced by these irradiations, one can capture a more complete picture of the above variations, which are characteristic of the place of origin of a sample. Thus, by using the methods disclosed herein, one can determine the place of origin of a sample more accurately (e.g., pinpointing the particular deposit or mine from which the sample is obtained).

In general, the irradiation locations are spaced from each other at a suitable distance (e.g., to be sufficiently large to characterize heterogeneity in the atomic composition of a sample or to make sure the sample from each location is not contaminated with the debris produced from previous irradiations). In some embodiments, the suitable distance can be at least 10 μm (e.g., at least 15 μm or at least 20 μm). In certain embodiments, the suitable distance can be at least 100 nm (e.g., at least 1 μm or at least 5 μm).

One can generally carry out step (b) by recording a spectrum of electromagnetic radiation emitted in response to each of the sample conversions (i.e., to form a plasma). In some embodiments, each spectrum is first detected by a detector (e.g., a spectrometer) and then recorded in an electronic processor (e.g., a computer). As a sample is irradiated with electromagnetic radiation (e.g., a laser) multiple times (e.g., at least 60 times) in step (a), multiple spectra are obtained from the sample. In general, each spectrum is detected and recorded prior to the next sample conversion by irradiation with electromagnetic radiation. In some embodiments, each spectrum is recorded with a spectral resolution sufficient to resolve the emission of electromagnetic radiation corresponding to atomic emission and one or more of isotopic emission, molecular emission, molecular isotopic emission, and spectral interference between atomic emissions from different atoms. In some embodiments, suitable spectral resolution can be at least 10,000 channels (e.g., at least 20,000 channels, at least 30,000 channels, at least 40,000 channels, at least 60,000 channels, at least 80,000 channels, at least 100,000 channels, at least 200,000 channels, or at least 300,000 channels) and up to as many as 400,000 channels or more. For example, a suitable spectral resolution can be 40,000 or 67,000 channels. Without wishing to be bound by theory, it is believed that using a high spectral resolution in the methods disclosed herein can resolve fine spectral lines or bands and therefore can increase the accuracy of the final results. For example, when a spectral resolution of as many as 400,000 channels is used in a spectral window between 195 nm and 1005 nm, spectral lines or bands having a width of about 2 pm can be resolved.

In some embodiments, after all spectra of a sample are recorded, the spectra can be scaled to a common unit of measurement. The scaling is generally achieved by using a piece of information preserving transformation (e.g., by dividing each spectrum channel by the mean value of the energy used to generate the spectra). The scaled spectra can then be compared among themselves to determine the number of different spectra (also referred to as "constituent signals"). The comparison can be performed (e.g., by an electronic processor such as a computer) as follows: One can first compare first and second scaled spectra from a sample. If these two scaled spectra are sufficiently similar, they are considered to be the same spectrum (i.e., the same constituent signal). If these two scaled spectra are substantially different, they are considered to be two different spectra (i.e., two different constituent signals). In some embodiments, to determine the similarity of two scaled spectra, one can use a matching algorithm (e.g., a weighted K-nearest neighbor algorithm) to compare the entire sequence of spectra for a sample to obtain a common reference spectrum (e.g., a centroid spectrum for all of the spectra for the sample). One can then compute the difference between each spectrum and the common reference spectrum. Subsequently, one can calculate the standard deviation of all of the differences. Two spectra are considered to be similar if the difference between each spectrum and the common reference spectrum is less than a given percent of the standard deviation of the differences from the common reference spectrum. One can then compare the third scaled spectrum with the first two scaled spectra. If the third scaled spectrum is sufficiently similar to one of the first and second scaled spectra, the third scaled spectrum is not considered to be a unique spectrum. If the third scaled spectrum is substantially different from either of the first and second scaled spectra, the third scaled spectrum is considered to be a unique spectrum (i.e., a different constituent signal). The process can be repeated until all scaled spectra collected from a sample have been compared with the other scaled spectra from the same sample. The unique spectra (each of which is in response to a different one of the sample conversions) can then be compiled to form a set of constituent spectra for the sequence. Each unique spectrum in a sequence is also referred to hereinafter as "a member" of the sequence. In general, a sequence can include one member (e.g., if the sample is perfectly homogenous) or two or more members (e.g., if the sample is heterogeneous). For many samples, the sequence typically includes at least 10 members (e.g., at least 15 members or at least 64 members).

Cluster technique algorithms such as those commercially available in MATLAB® toolboxes from MathWorks Inc. (Natick, Mass.) can be used to determine the constituent spectra in a sequence of spectra. For example, the weighted K-nearest neighbor algorithm described above can be used to identify spectra that define a common constituent when the weighted K-nearest neighbor differences are small enough.

In some embodiments, certain members of a sequence for a sample correspond to the spectra recorded in response to different parameters (e.g., different pulse energies, different pulse durations, different pulse wavelengths, or combinations thereof) for the pulses of electromagnetic radiation used to convert a portion of the sample into the plasma during the multiple conversions performed in step (a).

In some embodiments, certain members of a sequence for a sample correspond to the spectra recorded in response to different incident locations on the sample at which the pulse of electromagnetic radiation is irradiated to convert a portion of the sample into the plasma during the multiple conversions performed in step (a). In some embodiments, the different incident locations are sufficient to characterize heterogeneity in the atomic composition of a sample. For example, the different incident locations can be separated from one another by at least 10 μm (e.g., at least 15 μm or at least 20 μm). In some embodiments, certain members of a sequence for a sample correspond to the spectra recorded in response to different parameters for the pulses of electromagnetic radiation and different incident locations.

It is important to note that the methods disclosed herein utilize the entire spectrum of each spectrum in the sequence for a sample (e.g., a reference or unknown sample) without smoothing the spectrum or reducing the noise in the spectra by averaging spectra obtained from different irradiations and/or averaging spectra obtained from different irradiation locations and/or discarding low amplitude spectral lines and bands as noise. Without wishing to be bound by theory, it is believed that all of such information obtained from a sample is important, as it represents the "sequence" of the sample, and can be used to determine the place of origin of an unknown sample more accurately. By contrast, a conventional method generally uses only a portion of a spectrum from a sample, or averages a number of spectra to reduce noise, or discards low amplitude spectral lines as noise, which would lose valuable information about the sample.

After the sequence of spectra for a sample is obtained, step (c) can be performed by comparing the sequence with a sequence of spectra for each of multiple reference samples in a reference library. In general, to determine the place of origin of an unknown sample, the place of origin of each reference sample in the library is known.

Generally, the measured spectra of a sample are also scaled to a common unit of measurement by using a piece of information preserving transformation (e.g., by dividing each spectrum channel by the mean value of the pulse energy used to generate the spectra). This scaling is isomorphic so as to preserve relative variations within each spectrum.

In general, to establish a reference library for a geological material (e.g., a gemstone or a metal), reference samples can first be collected from deposits all around the world. To ensure a high degree of confidence in the place of origin of the geological material, it is desirable to document sufficient information about the material sample during collection, such as (1) the GPS coordinates of the location, (2) the time and date of collection, (3) the name and affiliation of the collector, (4) whether the sample is extracted from weathered rock, (5) whether the sample is extracted directly from a host rock, (6) the zone from which the sample is extracted, (7) the type of host rock, (8) whether the sample is extracted from mine tailings, the floor of the mine, or a river, (9) a description of the physical sample (e.g., its color, size, inclusions, or host rock), and (10) whether the sample is collected with other samples. In some embodiments, it is desirable to collect a statistically significant number of samples (e.g., at least 30 samples) from a particular mine in a deposit. In some embodiments, if a deposit has multiple mines, it is desirable to collect a statistically significant number of samples (e.g., at least 30 samples) from each mine. In some embodiments, if a mine has multiple zones containing the same geological material (e.g., a pegmatite), it is desirable to collect a statistically significant number of samples (e.g., at least 30 samples) from each zone. After collection, all samples are assigned an internal tracking number that can be used to track the samples to the collection event. The documents describing the parameters of collection are preserved with the physical samples, and rigorous chain-of-custody procedures are followed to ensure continuing integrity of the reference collection.

A sequence of spectra of each of the collected reference samples can then be obtained by carrying out steps (a) and (b) described above. In some embodiments, after the spectra of all collected reference samples are obtained, one can then apply a data analysis process (e.g., a matching algorithm such as a weighted K-nearest neighbor algorithm) to the reference samples to determine how similar/dissimilar the reference samples are to each other. In some embodiments, the weighting used in a weighted K-nearest neighbor algorithm is determined by a kernel density estimation function, such as that described in Webb, *Statistical Pattern Recognition,* 2002. In some embodiments, the data analysis process takes into account the distance between the data from two irradiation locations, where distance can be measured by the Mahalanobis metric, such as that described in Warren, et al., *Use of Mahalanobis Distance for Detecting Outliers and Outlier Cluster in Markedly Non-Normal Data,* 2011. Other aspects of the weighted K-nearest neighbor algorithm can be found, for example, in Viswanath, et al., *An improvement to k-nearest neighbor classifier,* 2011, IEEE Digital Library. In some embodiments, the data analysis process can start with a fixed set of test parameters (e.g., the number of data channels, the number of sample groups, the number of samples in each group, the distance between irradiation locations, the number of grid points (irradiation locations) in each sample, the shape of the grid as defined by the number of x-coordinates, y-coordinates and z-coordinates, the weights to be used in the weighting of the K-nearest neighbor algorithm, and/or the percent of the standard deviation of the differences between each spectrum and the common reference spectrum) and then start testing each reference sample at various incident locations on or in the sample. At the completion of this data analysis process, a profile of each test with respect to all of the other tests on or in that sample is defined. After the data analysis process is completed for all reference samples, the data obtained are included in a database. Analysis of the database can then be performed (e.g., by using a matching algorithm such as a weighted K-nearest neighbor algorithm described above) to determine how similar/dissimilar the reference samples are to each other. For example, if test results obtained from the surface of some of the samples are not similar to those obtained from the surface tests of the rest of the samples while test results obtained from a sub-surface in the samples are similar for all of the samples, one can conclude that there are two different types of coatings on the tested samples or that some of the tested samples lack a coating if test results obtained from the sub-surface and surface are similar for that set of samples. Based on the above analysis, samples having a common attribute (e.g., the same place of origin) can be included in a reference group.

In some embodiments, a single sample among a group of samples supposedly from the same place of origin may have very little similarity to the other samples in the group. This can imply that the assumption that this sample shares a common attribute with the other samples in the group may be false and may require further investigation before including this sample in a reference group. For example, the above incident can be caused by a human error (e.g., by misplacing a sample from a different location in that group).

In some embodiments, the above data analysis process can be applied to different reference groups in a reference library to determine the inherent dissimilarity between the groups. In general, no assumptions are made about the size or number of the reference groups that make up the reference library other than that each reference group has some attribute(s) that make it distinct from other groups. For example, the reference library can include only two reference groups, with one group having reference samples with a desirable property and the other group having reference samples lacking that desirable property. As another example, a reference library can include a large number of reference groups. For example, a reference library can be composed of emerald samples that are grouped based on the countries they came from.

In some embodiments, after a reference library is created, the sequence of spectra of an unknown sample can be compared with the sequence of spectra for each of the reference samples in the reference library (e.g., by using a data analysis process such as a weighted K-nearest neighbor algorithm) to determine whether the sequence of the unknown sample is similar to those of the samples in a reference group in the library. Suitable data analysis processes are discussed above. Based on the comparison, step (d) can be performed by using an electronic processor (such as a computer) to determine certain information about the sample. For example, if the sequence of the unknown sample is substantially similar to the sequence of one or more samples in a particular reference group, it can be concluded that the unknown sample belongs to this group. As another example, if the sequence of the unknown sample is significantly different from the samples in all of the reference groups in a library, it can be concluded that the unknown sample belongs to a new group not already in the library.

As noted above, in certain embodiments, the reference library can include only one reference sample. In such embodiments, the methods disclosed herein can be used to verify whether the unknown sample is the same as, or different from, the reference sample (e.g., for verification or authentication applications).

Figure 2:
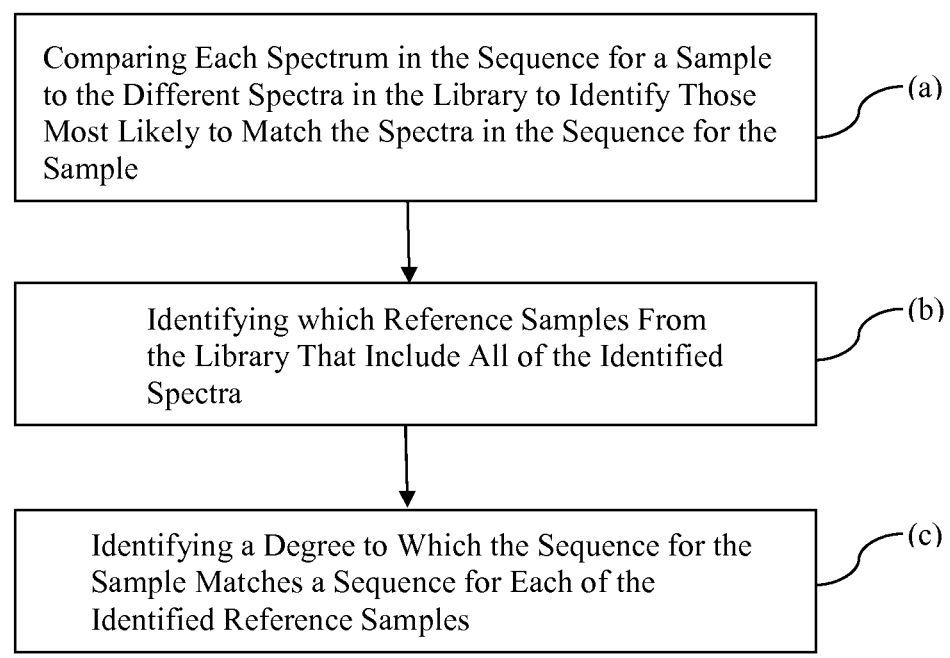
FIG. 2 is a flow chart showing a series of exemplary steps of performing step (c) in FIG. 1.

In some embodiments, after a reference library composed of mineral samples grouped based on their places of origin is created, the place of origin of an unknown sample of the same mineral can then be determined by comparing its sequence with the sequence of spectra for each of the reference samples in the reference library. In some embodiments, the comparison can be performed (e.g., by an electronic processor) to identify a degree to which the sequence of the sample matches a sequence for each of at least some of the reference samples in the library. For example, FIG. 2 is a flow chart showing a series of exemplary steps of performing this comparison. As shown in FIG. 2, the comparison can be performed by (a) comparing each spectrum in the sequence for the sample to the different spectra in the library to identify the different spectra from the library most likely to match the spectra in the sequence for the sample; (b) identifying which reference samples from the library include all of the identified spectra; and (c) identifying a degree to which the sequence for the sample matches a sequence for each of the identified reference samples. The above comparing and identifying step can be performed by using a data analysis process (e.g., the weighted K-nearest neighbor algorithm described above).

In some embodiments, the comparison by the electronic processor between the sequence of spectra for the sample being analyzed and the sequence of spectra for each of the reference samples includes comparing a probability distribution for the members of sequence of spectra in the sample being analyzed to a probability distribution for the members of the sequence of spectra for each of the reference samples. For example, the probability distribution for the sample being analyzed can be represented as a histogram indicating the number of times each member occurs in the sequence of spectra for the sample being analyzed and the probability distribution for the members of each reference sample can be represented as a histogram indicating the number of times each member occurs in the sequence of spectra for each reference sample. The electronic processor can then determine whether the sample being analyzed is one of the reference samples based on the degree to which this probability distribution for the sample being analyzed substantially matches this probability distribution for any one of the reference samples.

Figure 3:
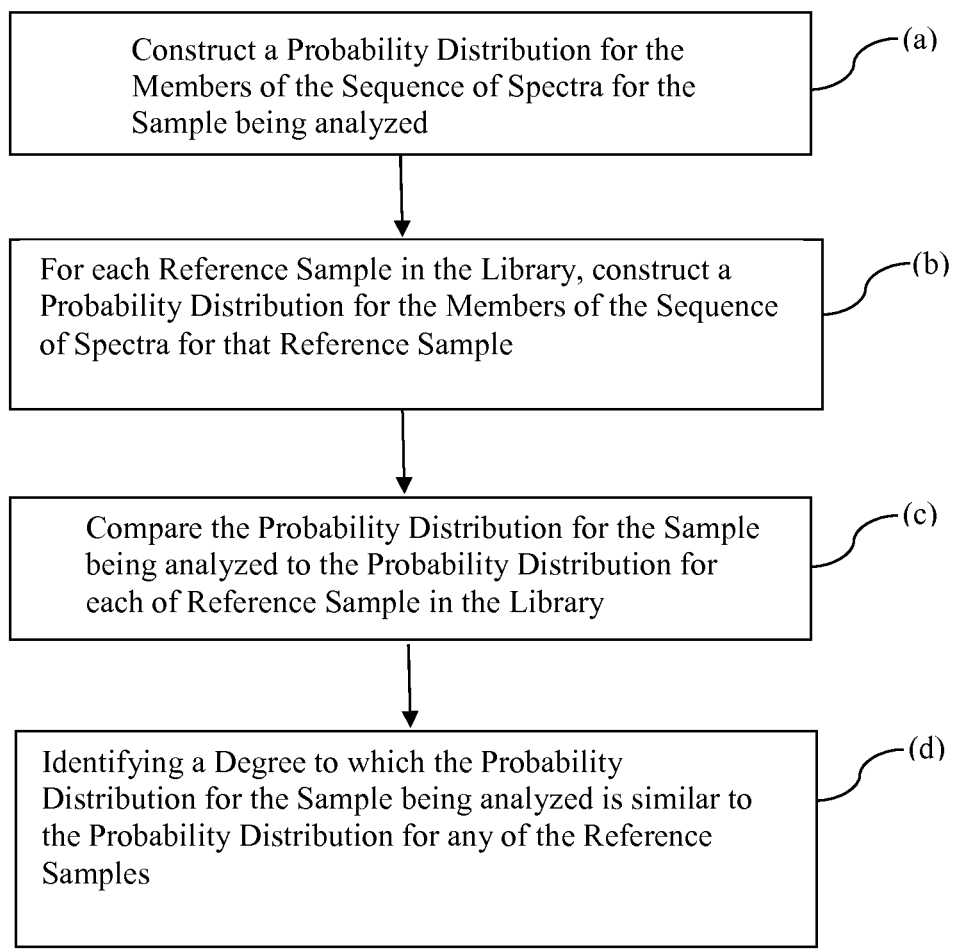
FIG. 3 is a flow chart showing another series of exemplary steps of performing step (c) in FIG. 1

This algorithm is shown schematically in FIG. 3 according to the following steps: (a) construct a probability distribution for the members of the sequence of spectra for the sample being analyzed; (b) for each reference sample in the library, construct a probability distribution for the members of the sequence of spectra for that reference sample; (c) compare the probability distribution for the sample being analyzed to the probability distribution for each of the reference samples in the library; and (d) identifying a degree to which the probability distribution for the sample being analyzed is similar to the probability distribution for any of the reference samples.

Without wishing to be bound by theory, it is believed that each mine or deposit has a unique petrogenetic signature, i.e., elemental and isotopic ratios unique to the petrogenesis of the deposit, and that reference samples from the same mine or deposit have a similar petrogenetic signature. Further, without wishing to be bound by theory, it is believed that one advantage of the methods disclosed herein is that the entire emission spectrum (including atomic emissions, isotopic emissions, molecular emissions, molecular isotopic emissions, and spectral interference between atomic emissions from different atoms) in response to each irradiation of a sample with electromagnetic radiation (e.g., laser) is utilized in the above data analysis to determine the similarity/differences between the samples in a library since only the entire emission spectrum of a sample can include all of the information in the petrogenetic signature of the sample. As a result, the methods disclosed herein can create a reference library containing reference samples with more precise location information and can identify the place of origin of an unknown sample more accurately than conventional methods, which typically use a selected window of spectrum, use atomic emissions only, or use averaged spectra to identify the place of origin of an unknown sample.

Figure 4:
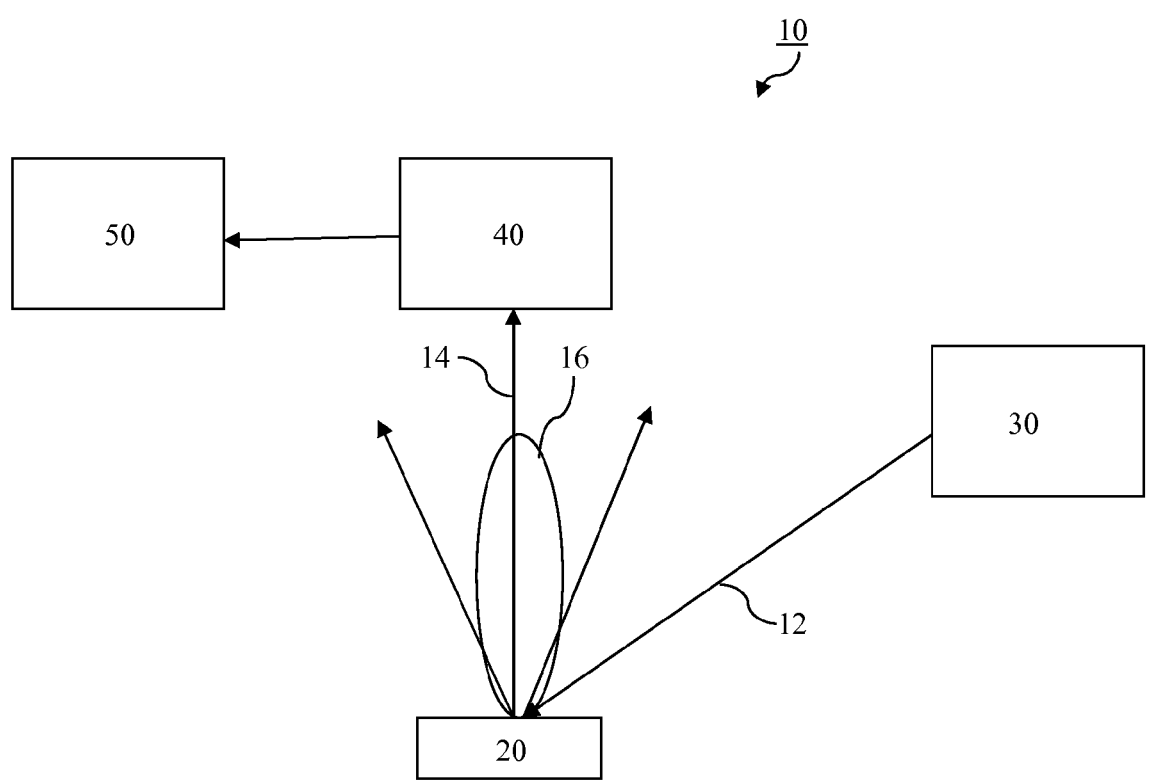
FIG. 4 is an illustration of an exemplary system for acquiring and analyzing an emission spectrum of a sample.

FIG. 4 illustrates an exemplary system of acquiring and analyzing an emission spectrum of a sample, which can be used to perform the methods discussed above (e.g., creating a reference library of various reference samples or determining the place of origin of an unknown sample). As shown in FIG. 1, system 10 includes a sample 20, an excitation source 30, a detector 40, and an electronic processor 50. Sample 20 can be those described above. Examples of excitation source 30 can be a laser (e.g., a Nd:YAG laser), an ion beam source (e.g., a liquid-metal ion source), an electron beam source, or an arc discharge lamp. Detector 40 can be a spectrometer (e.g., an Echelle spectrometer).

Although FIG. 4 depicts a certain geometric arrangement for excitation source 30 and detector 40 relative to sample 20, this is only by way of example. Accordingly, many different arrangements are possible for the relative positioning of excitation source 30, detector 40, and sample 20 as long as system 10 can acquire the emission spectra of sample 20. For example, in some embodiments, excitation source 30 can be placed at a location so that the incident irradiation is at a 90° angle to sample 20 and the emission from the sample is collected at a 45° angle from sample 20.

Electronic processor 50 can include one or more programmable computers and/or preprogrammed integrated circuits. It can further include one or more data storage systems (e.g., a memory and/or a storage element), one or more input devices (e.g., a keyboard), and one or more output devices (e.g., a display or a printer). Electronic processor 50 is generally designed to execute programs based on standard programming techniques. System 10 can also include other components (not shown in FIG. 1), such as a sample holder or a sample stage (with the capability of three-dimensional movement) and a camera (e.g., an ICCD camera). Furthermore, in some embodiments, some or all of the components of electronic processor 50 are directly coupled to detector 40. In other embodiments, some or all of the components of electronic processor 50 are physically separated from detector 40. For example, some or all of the processing can be carried out among one or more distributed processors that are located far from detector 40 (e.g., in the "cloud").

In some embodiments, the methods discussed above can be carried out by first emitting a pulse of electromagnetic radiation 12 (e.g., a high power laser pulse) from excitation source 30 to irradiate an incident location on sample 20 to create a plasma 16, which includes excited atomic elements. This step can be performed at multiple incident locations and/or multiple times at each incident location. Electromagnetic radiation 14 emitted from plasma 16 can then be collected (e.g., through fiber optics or a collimating lens) and detected by detector 40. The signals received from detector 40 can then be forwarded to electronic processor 50 to be recorded as emission spectra of the sample and analyzed (as described above) to determine the place of origin of the sample (e.g., by comparison to the emission spectra of reference samples in a reference library).

In some embodiments, the system shown in FIG. 1 can be a laser-induced breakdown spectroscopy (LIBS) system. In such embodiments, excitation source 30 can be a laser. In general, the laser has a sufficiently high energy to convert a portion of sample 20 to plasma 16. In some embodiments, the laser has a pulse energy of at least about 10 mJ (e.g., at least about 12 mJ, at least about 14 mJ, or at least about 16 mJ) and/or at most about 250 mJ (e.g., at most about 200 mJ, at most about 180 mJ, at most about 160 mJ, at most about 140 mJ, at most about 120 mJ, at most about 100 mJ, at most about 80 mJ, at most about 60 mJ, at most about 40 mJ, or at most about 20 mJ). In some embodiments, the pulse energy for each irradiation to sample 20 is substantially the same.

In some embodiments, the laser has a pulse duration of about 0.1 ps (e.g., at least about 1 ps, at least about 10 ps, or at least about 100 ps) and/or at most about 10 ns (e.g., at most about 5 ns, at most about 1 ns, or at most about 0.5 ns). In some embodiments, the pulse duration for each irradiation to sample 20 is substantially the same.

In some embodiments, a LIBS system can include two lasers with different wavelengths. For example, a LIBS system can include a 266 nm laser and a 1064 nm laser. Without wishing to be bound by theory, it is believed that the 266 nm laser can be used for analyzing transparent samples as it minimizes the traces or damage of testing to the samples and the 1064 nm laser can be used for analyzing translucent and opaque samples as it couples better with the surface of such a sample.

In some embodiments, a LIBS system can include a detector (e.g., a spectrometer) with sufficiently high spectral resolution and sufficiently wide spectral window. In some embodiments, the detector has at least 10,000 channels (e.g., at least 20,000 channels, at least 30,000 channels, at least 40,000 channels, at least 60,000 channels, at least 80,000 channels, at least 100,000 channels, at least 200,000 channels, or at least 300,000 channels) and up to as many as 400,000 channels or more. In some embodiments, the detector can have 40,000 or 67,000 channels. In some embodiments, the detector can resolve features or peaks finer than 0.1 nm (e.g., finer than 0.06 nm or finer than about 0.02 nm). In some embodiments, the detector can have a spectral window between 195 nm and 1005 nm. For example, with as many as 400,000 channels, the spectral resolution is finer than about 2 pm over the spectral window between 195 nm and 1005 nm.

Other components in a LIBS system are generally known in the art, such as those described in U.S. Pat. Nos. 5,751,416; 7,195,371; and 7,557,917; Cremers et al., *Handbook of Laser-Induced Breakdown Spectroscopy*, John Wiley & Sons Ltd, 2006; and Miziolek et al., *Laser-Induced Breakdown Spectroscopy (LIBS) Fundamentals and Applications*, Cambridge University Press, 2006.

In general, LIBS systems offer various advantages over other analytical techniques for determining the place of origin of an unknown sample. For example, LIBS systems are easy to use (e.g., requiring minimal sample preparation) and relatively inexpensive. In addition, LIBS systems can be portable so they can be used outside of a laboratory (e.g., at a field site). LIBS systems are available from commercial sources, such as Photon Machines, Inc. (Redmond, Wash.) and Applied Spectra (Fremont, Calif.).

In some embodiments, a LIBS system can be used to analyze a reference or unknown sample as follows. Prior to a sample being analyzed, the laser in the LIBS system is generally warmed up (e.g., by irradiating pulses of laser without using the emitted radiation for analysis) for a sufficient period of time (e.g., at least 10 minutes). After the laser is warmed up, a calibration sample can be analyzed to ensure the repeatability of results (e.g., from day to day). All data collected on calibration samples can be saved along with photos of the calibration sample. If the analysis of the calibration sample does not fall within tolerated levels, a diagnostic test can be performed to ensure the LIBS system is working correctly. If the analysis of the calibration sample falls within tolerated levels, the analysis of a reference or unknown sample can begin.

In general, sample 20 is cleaned prior to being analyzed by a LIBS system. For example, sample 20 can be cleaned by a medical alcohol wipe, and followed by washing with an alcohol (e.g., isopropyl alcohol). After sample 20 is cleaned, it can be mounted on a sample stage in a mounting material (e.g., a mineral tack) for testing in a LIBS system. The mounting material is generally changed when a different sample is analyzed to reduce the risk of cross contamination.

Once a sample is cleaned and mounted, it can be brought into focus on the sample stage. In some embodiments, when the sample is optically in focus on a computer monitor connected to a camera in the LIBS system, it is also in focus for the laser beam to form a plasma. Prior to irradiating a laser pulse to the sample to generate a plasma, a flow of a high purity inert gas (e.g., 99.999% pure argon) can be turned on to cover the surface of the sample to be analyzed. Without wishing to be bound by theory, it is believed that, due to extremely small variations present in geological materials, using a pure inert gas (e.g., argon) to cover the sample surface can avoid contamination and variability from atmospheric air.

In some embodiments, during the analysis process, a certain number (e.g., at least four) of pictures of the sample can be taken. For example, one can take two pictures of the sample before analysis and two pictures after analysis. In some embodiments, prior to the analysis of the sample, one can take a picture of the sample in focus on the sample stage and label it as a "before" picture without a "grid." After selecting an area on the sample to be analyzed and superimposing a grid on the sample but prior to analyzing the sample, one can then take a second picture of the sample (which is still in focus and sitting on the sample stage) and label it as a "before" picture with a "grid." Without wishing to be bound by theory, it is believed that it can be important to take pictures prior to sample analysis as a sample may have very small variations (e.g., inclusions or surface irregularities) that may be completely converted into a plasma upon irradiation with a laser. In that case, the variations may produce anomalies in the emission spectra of the sample, which can be explained by comparing the pictures taken before and after sample analysis.

In some embodiments, based on the geological material being analyzed, one can select the spacing between irradiation or incident locations on a sample. The irradiation of a sample by a laser that produces a plasma is also known as a "shot." In some embodiments, the spacing between shot locations can be at least 10 µm. However, this spacing can increase (e.g., to at least 15 µm or at least 20 µm), for example, based on how a sample responds to the conversion from a solid to a plasma. For example, when the sample is gold, the spacing between shot locations is often more than 250 µm as the gold can be completely ablated for a diameter of about 200 µm. In certain embodiments, the spacing can be decreased to at least 100 nm (e.g., at least 1 µm or at least 5 µm).

In some embodiments, prior to irradiating laser pulses to a sample, other analytical parameters (e.g., laser wavelength, laser power, or spectral delay) in a LIBS system can be set. Based on the geological material analyzed, these parameters can be varied slightly to capture the petrogenetic signature of the sample. In some embodiments, prior to selection of analytical parameters, an analytical parameter determination test can be performed. This test can include analyzing multiple samples of the same mineral from different locations. The variable analytical parameters can be changed (e.g., one at a time) to evaluate a large number (e.g., as many as 300) of different permutations before a final set of analytical parameters is established for the mineral.

As an example, when the mineral beryl is analyzed, one can use a LIBS system having a 266 nm laser, a laser power of 90% (which corresponds to between 12 and 20 mJ), a spectral delay of 1.5 µs, and a gain of 150 µs. All of the analytical parameters used during the analysis process can be documented, including the size of the superimposed grid (e.g., 2 excitation locations by 5 excitation locations) and the location of the initial shot. Based on the movement allowed by the LIBS system used in this embodiment, all analyses can be collected at irradiation locations from left to right and then from top to bottom. The collection of the irradiation locations can be important as it helps to determine the number of constituent signals in a sample. In some embodiments, the depth of analysis can vary greatly based on the laser power used. However, the depth of analysis can stay relatively constant within a set of selected analytical parameters.

In general, once all of the analytical parameters of a LIBS system are set, the methods disclosed herein can be performed to analyze a reference or unknown sample.

The contents of all publications cited herein (e.g., patents, patent application publications, and articles) are hereby incorporated by reference in their entirety.

The following example is illustrative and not intended to be limiting.

EXAMPLE 1

Two hundred and seventy beryl ($Be_3Al_2Si_6O_{18}$) crystals (var. emeralds) from 9 different locations in 8 different countries were analyzed using Laser Induced Breakdown Spectroscopy (LIBS). Thirty individual crystals from each location were studied. The countries where beryl samples were obtained are Afghanistan (AFG), Brazil (BRA), Colombia (COL), Mozambique (MOZ), Pakistan (PAK), South Africa (ZAF), Zambia (ZMB) and Zimbabwe (ZWE). Two separate and unique deposits in Colombia were analyzed in this study.

A Photon Machines Insight LIBS system was used for this study. Emission spectra from 30 laser excitations (shots) were collected at 30 unique excitation locations on the surface of each sample. For each excitation location analyzed, a single cleaning shot (an excitation on the sample surface without the emission generated from the excitation being collected) was performed prior to the collection shot (an excitation on the sample surface from which the emission generated from the excitation is collected). Sample ablation for the experiment reported here was achieved using a Nd:YAG laser operating at 266 nm with a repetition rate of 1 Hz, a typical pulse energy of 13 mJ and a pulse width of about 6 ns. The laser beam was focused onto the surface of the sample. A flow of 99.9% pure argon covered the surface of the sample to reduce contamination from ambient air. A second lens was used to collect the emission from the laser induced plasma via a fiber optic cable coupled to an Echelle spectrometer with a spectral resolution of 0.02 nm and a spectral range of 200.02-1000.02 nm (40,000 channels). At a delay of 1 µs after the laser pulse, the dispersed emission was recorded for a duration of 10 µs by an Intensified Charge-Coupled Device (ICCD) at a gain setting of 150 µs. The emission spectrum for each shot was saved independently, without averaging, to an electronic processor using the Chromium software that came as a part of the Photon Machines Insight LIBS system.

After data were collected on all 270 beryl samples using the experimental setup mentioned above, a blind test was performed. The data were analyzed using both an inventive method described herein ("the M2S method") and a conventional partial least squares discriminant analysis (PLSDA). The PLSDA analysis was performed by a private third party (PTP). The PTP was not instructed to use PLSDA but to use any of the traditional analysis techniques typically used in the evaluation of LIBS data. The PTP is well respected and known to those in the art. The PTP was selected because they had worked previously on geological material determination problems containing far less robust data sets and they are considered experts in the field of "complex" LIBS data analysis.

Both the PTP and the M2S group were provided identical raw spectral data from the LIBS analysis. The PTP used only "every 5$^{th}$ wavelength" in the PLSDA (disregarding 80% of the data available for analysis.) A simple 50/50 split of the data into separate sets for training and evaluation was used by the PTP. The PTP created a reference library using data from 15 samples from each site. The blind samples (containing data from the 15 remaining samples) were tested and matched to the samples in the reference library. It was determined by the PTP that performance of the predictive model generated using these data peaked around 20 latent variables.

The group using the M2S method processed all of the data provided in the method described earlier. Specifically, the raw spectral data for each sample (comprising 40,000 channels), be it a reference sample or an unknown sample, was converted into sequences of scaled spectra using the method described earlier in this application. The reference library consisted of the sequences of the scaled spectra of samples from known origins.

Each sequence for an unknown sample was compared to every known sequence in the reference library using a 270-fold leave one sample (sequence) out test design. A leave one out methodology begins by removing the first sample's sequences from the reference library and recreating the reference library from the sequences of the remaining 269 samples. This process was repeated for every sample in the test.

The comparison was made based on a weighted K-nearest neighbor algorithm which produced a table containing the distance between the unknown samples sequences and every known sequence in the reference library. The table related the distance between the unknown sample and all of the known samples based on the distance between their respective sequences of scaled spectra. The table was ordered from the smallest distance to the largest distance from the unknown sample's sequences to the known samples' sequences. Subsequently, each distance was used to compute a score, which was based on the relationship of the distance between the unknown and known sequences of scaled spectra. The smaller the distance between the unknown and known sequences of scaled spectra, the greater the value of the score. This is known as the weighting function. A second table was created that related the score that each known sample received. This table was ordered from the largest score to the smallest score. The known sample with the highest score was identified as the closest match to the unknown sample. Thus, the origin of the known sample identified as having the closest match was assigned to the unknown sample.

The accuracy of the matching in the M2S and PTP groups is summarized in Table 1 below.

TABLE 1

| Country | M2S Method | PLSDA |
|---------|------------|-------|
| AFG | 98.0% | 80.0% |
| BRA | 98.0% | 58.0% |
| COL | 100.0% | 97.3% |
| MOZ | 98.0% | 88.7% |
| PAK | 98.0% | 48.7% |
| ZAF | 99.0% | 96.0% |
| ZMB | 95.0% | 98.7% |
| ZWE | 97.0% | 44.0% |
| Average | 98% | 76% |

As shown in Table 1, the M2S method provided an average of 98% accuracy in determining country of origin, while PLSDA provided an average accuracy of only 76%.

After the conclusion of the study, the PTP was asked why they had disregarded 80% of the data. The PTP indicated that an excessive amount of data had been provided and that using any conventional data analysis techniques with that much data would require too much processing time.

EXAMPLE 2

90 coupons of 17-4 Stainless Steel, all initially originating from the same bar, but with three different conditions (heat treatments), were analyzed using Laser Induced Breakdown Spectroscopy (LIBS). Thirty individual coupons from each treatment were studied. The treatments studied were Condition A; Condition H900, and Condition H1150. The material analyzed in this study did not come with certificates, thus the specifics of the heat treatment can not be certified. In general the following is true for each of the conditions studied.

Condition A is the original annealed condition for the bar, no heat treatment or aging. Condition H900 was age hardened at 482° C. for 1 hour, and then air cooled. Condition H1150 was heated at 760° C. for 2 hours and air cooled, then heated at 621° C. for 4 hours, and then air cooled.

A Photon Machines Insight LIBS system was used for this study. Emission spectra from 64 laser excitations (shots) were collected at 64 unique excitation locations on the surface of each sample. For each excitation location analyzed, a single cleaning shot (an excitation on the sample surface without the emission generated from the excitation being collected) was performed prior to the collection shot (an excitation on the sample surface from which the emission generated from the excitation is collected). Sample ablation for the experiment reported here was achieved using a Nd:YAG laser operating at 1064 nm with a repetition rate of 1 Hz, a typical pulse energy of 90 mJ and a pulse width of 6 ns. The laser beam was focused onto the surface of the sample. A flow of 99.9% pure argon covered the surface of the sample to reduce contamination from ambient air. A second lens was used to collect the emission from the laser induced plasma via a fiber optic cable coupled to an Echelle spectrometer with a spectral resolution of 0.02 nm and a spectral range of 200.02-1000.02 nm (40,000 channels). At a delay of 1.25 µs after the laser pulse, the dispersed emission was recorded for a duration of 10 µs by an Intensified Charge-Coupled Device (ICCD) at a gain setting of 200 µs. The emission spectrum for each shot was saved independently, without averaging, to an electronic processor using the Chromium software that came as a part of the Photon Machines Insight LIBS system.

Using the experimental setup described above, each sample was analyzed 64 times; for a total of 1920 collection shots for each condition. A total of 5760 collection shots across all three conditions were collected. The raw spectral data for each sample (comprising 40,000 channels), was converted into sequences of scaled spectra using the method described earlier in this application. The reference library consisted of the sequences of the scaled spectra of samples.

Each sequence for an unknown sample was compared to every known sequence in the reference library using a 90-fold leave one sample (sequence) out test design. A leave one out methodology begins by removing the first sample's sequences from the reference library and recreating the reference library from the sequences of the remaining 89 samples. This process was repeated for every sample in the test.

The comparison was made based on a weighted K-nearest neighbor algorithm which produced a table containing the distance between the unknown samples sequences and every known sequence in the reference library. The table related the distance between the unknown sample and all of the known samples based on the distance between their respective sequences of scaled spectra. The table was ordered from the smallest distance to the largest distance from the unknown sample's sequences to the known samples' sequences. Subsequently, each distance was used to compute a score, which was based on the relationship of the distance between the unknown and known sequences of scaled spectra. The smaller the distance between the unknown and known sequences of scaled spectra, the greater the value of the score. This is known as the weighting function. A second table was created that related the score that each known sample received. This table was ordered from the largest score to the smallest score. The known sample with the highest score was identified as the closest match to the unknown sample. Thus, the Condition of the known sample identified as having the closest match was assigned to the unknown sample.

TABLE 2

| Condition of 17-4 Stainless Steel | M2S Method |
| --- | --- |
| Condition A | 96.7% |
| Condition H900 | 98.9% |
| Condition H1150 | 97.8% |
| Average | 97.8% |

As shown in Table 2, the M2S method provided an average of 97.8% accuracy in determining the condition of 17-4 stainless steel.

As discussed earlier, peaks in the data were initially thought to merely represent atomic emissions. However, it has now been shown that peaks not only contain atomic emissions, but also represent isotopic, molecular, and molecular isotopic emissions. Some data in the peaks may be produced by spectral interference. For example the concentrations of Mg and Na may not be accurate quantitative values. Rather, due to the interaction in the plasma, some concentrations of one element, say Na, appear to be greater than what is actually present, and Mg appears to have a lower concentration than what is actually present, due to the spectral interference phenomenon. Moreover, the shape of the peaks is critical, because the shape may represent re-absorption of the emitted element. This is ordinarily seen as a flat top of a peak rather than a point.

Figure 5:
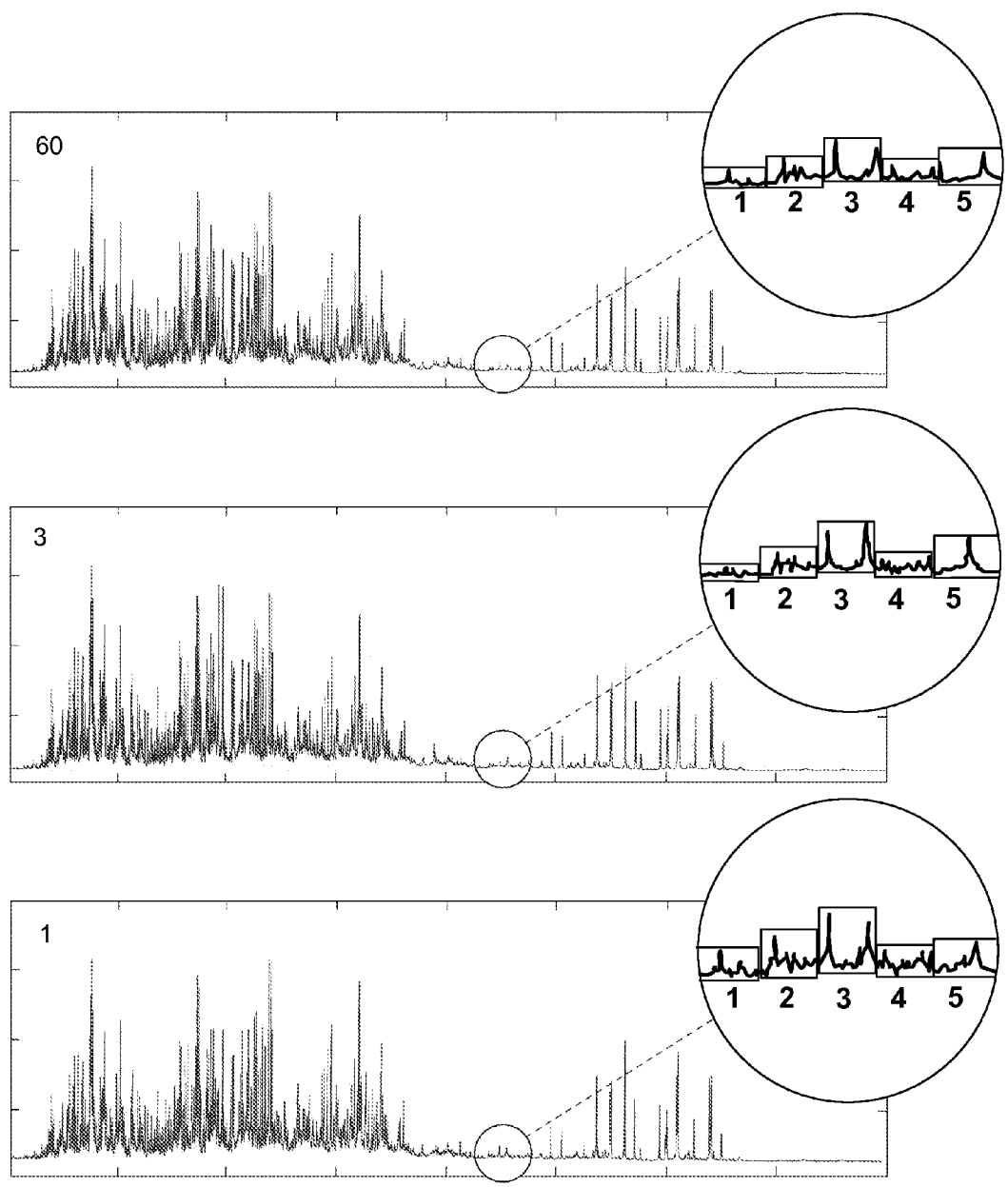
FIG. 5 shows three graphs showing constituent spectra for sample of 17-4 Stainless Steel subjected to a specific processing condition.

FIG. 5 displays three graphs (Q-set). Each graph is a visual representation of the different members of the sequence that were found in a sample of the Condition H900 17-4 Stainless Steel. A magnified view of approximately 1600 channels of the spectrum of the sequence member is provided to the right in a circle. Each area magnified is the same section of the sequence. The top graph represents the Prime-Q (2Qn4), this is the primary constituent found in all of the data for the 17-4 Stainless Steel. The second graph (2Qn2) and the third graph (2Qn7) represent two other members of the sequence for the Condition H900 samples.

Across all three conditions, a total of 9 different members of the sequence were seen. Table 3 shows the frequency of each condition. Only three members of the sequence were seen in any one sample at any given time.

TABLE 3

| Condition | 2Qn1 | 2Qn2 | 2Qn3 | 2Qn4 (Prime-Q) | 2Qn5 | 2Qn6 | 2Qn7 | 2Qn8 | 2Qn9 |
| --- | --- | --- | --- | --- | --- | --- | --- | --- | --- |
| A | 0 | 11 | 21 | 1847 | 20 | 14 | 7 | 0 | 0 |
| H900 | 4 | 23 | 13 | 1847 | 15 | 2 | 9 | 5 | 2 |
| H1150 | 15 | 15 | 6 | 1848 | 13 | 2 | 6 | 8 | 7 |
| Total # of Occurrences | 19 | 49 | 40 | 5542 | 48 | 18 | 22 | 13 | 9 |

In the case of the Condition A samples, the primary constituent (2Qn4) appeared 5542 out of 5760 times. The 2Qn1, 2Qn8, and 2Qn9 constituents did not appear at all in the Condition A samples. The 2Qn2 constituent appeared 11 times, the 2Qn3 appeared 21 times, the 2Qn5 constituent appeared 20 times, the 2Qn6 constituent appeared 14 times, and the 2Qn7 constituent appeared 7 times.

In the case of the Condition H900 samples and the Condition H1150 samples, the sequence of spectra produced the same members: 2Qn1, 2Qn2, 2Qn3, 2Qn4, 2Qn5, 2Qn6, 2Qn7, 2Qn8, and 2Qn9. However, the probability distribution for these members differed from that obtained from the Condition A sample. Specifically, the 2Qn1, 2Qn8, and 2Qn9 constituents were found in the Condition H900 (4 occurrences) and the Condition H1150 (15 occurrences) samples but were absent from the Condition A samples. The 2Qn2 constituent appeared 23 out of 5760 times in Condition H900 and 15 out of 5760 times in Condition H1150. The 2Qn3 constituent appeared 13 out of 5760 times and 2Qn4 appeared 1847 out of 5760 times in Condition H900. In this same condition, the 2Qn5 constituent appeared 15 out of 5760 times, 2Qn6 appeared 2 out of 5760 times, 2Qn7 appeared 9 out of 5760 times, 2Qn8 appeared 5 out of 5760 times, and 2Qn9 appeared 2 out of 5760. In the case of the Condition H1150 samples, the sequence of spectra produce the same primary constituent, 2Qn4, which appeared 1848 out of 5760 times. The 2Qn1 constituent appeared 15 out of 5760 times and 2Qn2 appeared 15 out of 5760 times. In this same condition, the 2Qn3 constituent appeared 6 out of 5760 times and 2Qn5 appeared 13 out of 5760. The 2Qn6 and 2Qn7 constituents appeared 2 and 6 out of 5760 times, respectively, and the 2Qn8 and 2Qn9 constituents appeared 8 and 7 out of 5760 times, respectively. By comparing the probability distribution of the member for all three types of samples, the samples could be distinguished among one another as set forth in Table 2 above.

Referring again to FIG. 5, five unique areas within the magnified area have been selected and highlighted. These areas are meant to help visually display the differences in the data that the algorithm identifies. One will notice that the location, size, and shapes of the peaks in each of these three boxes are unique, and the algorithm is able to identify these differences. In Box One of each of the three graphs, one will notice that the height of the first peak in the bottom graph (2Qn7) is greater than that of the same peak in graphs 2Qn4 and 2Qn2. The second peak in Box One is highest in the first graph (2Qn4) and almost non-existent in the third (2Qn7). As one continues to visually inspect the data, numerous differences can be seen. These differences characterize each member of the sequence.

Other embodiments are within the scope of the claims.

What is claimed is:

1. A method for analyzing a sample, the method comprising:
   converting a portion of the sample into a plasma multiple times;
   recording a spectrum of electromagnetic radiation emitted in response to each of the sample conversions to define a sequence of spectra for the sample, wherein the sequence of spectra for the sample comprises multiple members, and each member of the sequence corresponds to the spectrum recorded in response to a different one of the sample conversions;
   using an electronic processor to compare the sequence of spectra for the sample to a sequence of spectra for each of at least one reference sample in a reference library, wherein the sequence of spectra for each reference sample comprises multiple members, and the comparing comprises comparing the number of times each member occurs in the sequence of spectra for the sample with the number of times each member occurs in the sequence of spectra for each reference sample; and
   using the electronic processor to determine information about the sample based on the comparison to the at least one reference sample in the library.

2. The method of claim 1, wherein a pulse of electromagnetic radiation is used to convert the sample into the plasma for each of the multiple times.

3. The method of claim 2, wherein members of the sequence for the sample correspond to the spectra recorded in response to different parameters for the pulse of electromagnetic radiation used to convert the portion of the sample into the plasma during the multiple times.

4. The method of claim 3, wherein the different parameters comprise different pulse energies, different pulse durations, different pulse wavelengths, or combinations thereof.

5. The method of claim 2, wherein members of the sequence for the sample correspond to the spectra recorded in response to different incident locations on the sample for the pulse of electromagnetic radiation used to convert the portion of the sample into the plasma during the multiple times.

6. The method of claim 5, wherein the different incident locations are separated sufficiently to characterize heterogeneity in the atomic composition of the sample.

7. The method of claim 5, wherein the different locations are separated from one another by at least 10 μm.

8. The method of claim 5, wherein the different incident locations comprises at least 10 different locations.

9. The method of claim 2, wherein members of the sequence for the sample correspond to the spectra recorded in response to combinations of different parameters for the pulse of electromagnetic radiation used to convert the portion of the sample into the plasma during the multiple times and different incident locations on the sample for the pulse of electromagnetic radiation used to convert the portion of the sample into the plasma during the multiple times.

10. The method of claim 2, wherein members of the sequence for the sample correspond to the spectra recorded in response to the pulse of electromagnetic radiation used to convert the portion of the sample into the plasma during the multiple times that has a fixed spectral delay.

11. The method of claim 1, wherein the conversion of the sample into the plasma causes the sample to emit electromagnetic radiation indicative of atomic emissions.

12. The method of claim 1, wherein the conversion of the sample into the plasma causes the sample to emit electromagnetic radiation indicative of one or more of isotopic emissions, molecular emissions, molecular isotopic emissions, and spectral interference between atomic emissions from different atoms in the sample.

13. The method of claim 1, wherein each spectrum is recorded with a spectral resolution sufficient to resolve the emission of electromagnetic radiation corresponding to atomic emission and one or more of isotopic emission, molecular emission, molecular isotopic emission, and spectral interference between atomic emissions from different atoms.

14. The method of claim 1, wherein each spectrum is measured with a spectral resolution finer than 0.1 nm.

15. The method of claim 1, wherein each spectrum is measured over a range including from 195 nm to 1005 nm.

16. The method of claim 1, wherein the sequence of spectra for the sample comprises members corresponding to all of the different spectra recorded for the sample during the multiple times.

17. The method of claim 16, wherein the comparison by the electronic processor comprises comparing a probability distribution for the members of the sequence of spectra for the sample being analyzed to a probability distribution for members of the sequence of spectra for each of the reference samples.

18. The method of claim 17, wherein the probability distribution for the sample being analyzed is represented as a histogram indicating the number of times each member occurs in the sequence of spectra for the sample being analyzed and the probability distribution for the members of each reference sample is represented as a histogram indicating the number of times each member occurs in the sequence of spectra for each reference sample.

19. The method of claim 1, wherein the comparison by the electronic processor comprises identifying a degree to which the sequence for the sample matches a sequence for each of the at least one reference sample in the library.

20. The method of claim 19, wherein identifying the degree to which the sequence for sample matches a sequence for each of the reference samples comprises comparing a probability distribution for the members of the sample being analyzed to a probability distribution for members of the sequence of spectra for each of the reference samples.

21. The method of claim 19, wherein identifying a degree comprises:
   comparing each spectrum in the sequence for the sample to the different spectra in the library to identify the different spectra from the library most likely to match the spectra in the sequence for the sample;
   identifying which reference samples from the library comprise all of the identified spectra; and
   identifying a degree to which the sequence for the sample matches a sequence for each of the identified reference samples.

22. The method of claim 1, wherein the reference library is made by:
  providing information about the identity of each reference sample;
  converting a portion of each reference sample into a plasma multiple times; and
  recording a spectrum of electromagnetic radiation emitted from each reference sample in response to each of the reference sample conversions to define a sequence of spectra for each reference sample, wherein each member of the reference sample sequence corresponds to the spectrum recorded in response to a different one of the reference sample conversions.

23. The method of claim 22, wherein members of each reference sample sequence correspond to the spectra recorded in response to combinations of different parameters for a pulse of electromagnetic radiation used to convert the portion of each reference sample into the plasma during the multiple times and different incident locations on each reference sample for the pulse of electromagnetic radiation used to convert the reference sample into the plasma during the multiple times.

24. The method of claim 1, wherein the at least one reference sample comprises multiple reference samples.

25. The method of claim 24, wherein the multiple reference samples comprises metal alloys having common elemental compositions and different processing protocols.

26. The method of claim 1, wherein the sample being analyzed and the reference sample comprise metal alloys having a common elemental composition, and wherein the information determined by the electronic processor is whether the sample being analyzed has been subjected to a specific processing protocol corresponding to one of the reference samples.

27. The method of claim 1, wherein the information about the sample comprises an identity for the sample.

28. The method of claim 1, wherein the information about the sample comprises a provenance for the sample.

29. A system for analyzing a sample, the system comprising:
  an excitation source for converting a portion of the sample into a plasma multiple times;
  a spectrometer configured to record a spectrum of electromagnetic radiation in response to each of the sample conversions to define a sequence of spectra for the sample, wherein the sequence of spectra for the sample comprises multiple members, and each member of the sequence corresponds to the spectrum recorded in response to a different one of the sample conversions; and
  an electronic processor configured to compare the sequence of spectra for the sample to a sequence of spectra for each of at least one reference sample in a reference library and determine information about the sample based on the comparison to the at least one reference sample in the library, wherein the sequence of spectra for each reference sample comprises multiple members, and the comparing comprises comparing the number of times each member occurs in the sequence of spectra for the sample with the number of times each member occurs in the sequence of spectra for each reference sample.

* * * * *